United States Patent [19]

Schwartzenfeld

[11] Patent Number: 5,381,802

[45] Date of Patent: Jan. 17, 1995

[54] SHIELD FOR PREVENTING CAUTERY BURNS

[76] Inventor: Ted H. Schwartzenfeld, 4855 Rolling Ridge Rd., West Bloomfield, Mich. 48323

[21] Appl. No.: 73,134

[22] Filed: Jun. 7, 1993

[51] Int. Cl.⁶ .............. A61F 11/00; A61B 19/00; A61B 19/08
[52] U.S. Cl. ................... 128/857; 128/849; 128/853
[58] Field of Search ............... 128/849, 850, 851, 852, 128/853, 854, 855, 856, 857; 2/7, 81, 206

[56] References Cited

U.S. PATENT DOCUMENTS

| | | |
|---|---|---|
| 3,455,302 | 7/1969 | Liloia et al. .............. 128/849 |
| 3,930,497 | 1/1976 | Krebs et al. .............. 128/853 |
| 4,573,217 | 3/1986 | Reed ............................ 2/7 |
| 4,604,998 | 8/1986 | Bellina ....................... 128/849 |
| 4,901,738 | 2/1990 | Brink et al. .............. 128/849 |
| 4,966,140 | 10/1990 | Dunsch-Herzberg . |
| 4,969,473 | 11/1990 | Bothwell ................... 433/136 |
| 5,025,506 | 6/1991 | Huang . |
| 5,042,507 | 8/1991 | Dowdy ....................... 128/857 |
| 5,050,241 | 9/1991 | Flowers et al. ............. 2/81 |
| 5,082,721 | 1/1992 | Smith, Jr. et al. ......... 2/81 |
| 5,140,997 | 8/1992 | Glassman ................... 128/857 |
| 5,197,493 | 3/1993 | Grier-Idris ............... 128/849 |
| 5,225,236 | 7/1993 | Keresch et al. ........... 128/849 |
| 5,226,815 | 7/1993 | Bowman ..................... 433/137 |

OTHER PUBLICATIONS

Brittence, John C., Ed. *Engineering Plastics & Composites*, Oh, ASM International, 1990, Section II pp. 9 & 10 TP1132-E54.

*Primary Examiner*—Robert A. Hafer
*Assistant Examiner*—Michael O'Neill
*Attorney, Agent, or Firm*—Reising, Ethington, Barnard, Perry & Milton

[57] ABSTRACT

A drapery shield (10) for preventing cautery burns to the skin of a patient about the area to be cauterized has a first or upper layer (12) which is formed from a fire-retardant material and a second or underdrape layer (14) which is formed from a non-porous material. The two layers are bonded to each other, such as by sonic welding or the like. An adhesive tape (15) or similar material is used to removably adhere the shield to the skin of a patient about the area to be cauterized. The fire-retardant material prevents cautery burns or the like to the patient.

7 Claims, 2 Drawing Sheets

SHIELD FOR PREVENTING CAUTERY BURNS

TECHNICAL FIELD OF THE INVENTION

The present invention relates to surgical sheets. Even more particularly, the present invention pertains to drape sheets. Even more particularly, the present invention concerns shields for preventing cautery burns.

BACKGROUND OF THE INVENTION

Heretofore, the prior art has proposed various surgical masks and hoods to protect either the surgeon or the patient from various medical environments.

For example, U.S. Pat. No. 4,966,140 teaches a surgical mask to prevent contact between the surgeon and the secreted body fluids of the patient.

Other representative prior art can be found in U.S. Pat. Nos. 1,990,199; 3,885,558; 5,007,114; 5,025,506; and 4,589,408.

It is to be appreciated that each and every one of the prior art references is intended to perform a specific function, such as preventing bacterial contact.

As is known to those skilled in the art to which the present invention pertains, electro-cauterization involves the use of a cautery, which creates the potential for significant burns to the skin of a patient surrounding the area to be cauterized. During the surgical procedure it is quite possible to touch the dermal layers with the cautery, thereby, inflicting a serious burn.

What is needed is a drop sheet which functions as a shield to prevent such burns.

SUMMARY OF THE INVENTION

In accordance with one aspect of the present invention, there is provided a drapery shield for preventing cautery burns to the skin of a patient about the area to be cauterized, which generally comprises; first layer comprising a fire-retardant material; a second layer or underdrape comprising a non-porous material; and an adhesive for removably adhering the shield to the face of a patient and openings through the sheet to allow operating on the patient through the openings.

In accordance herewith the first or upper layer is that which is exposed to the environment and is, generally, a fire-retardant foam, such as a polyurethane foam, or the like.

The second layer is a non-porous layer, such as a polyethylene or polypropylene-type material. The polyurethane foam is bonded to the second layer by any suitable method, such as sonic welding, heat welding, or the like. The non-porous layer functions as an underdrape and covers the area around the opening to which the cautery will be applied, such as the mouth of the patient.

A tape or similar material is adhered to the under drape to provide for the removable affixation of the shield to the are about to be cauterized. In one embodiment, the tape is placed only about the periphery of the openings.

BRIEF DESCRIPTION OF THE DRAWING

Reference is now made to the accompanying drawings in which.

DESCRIPTION OF THE PREFERRED EMBODIMENT

Figure 1:
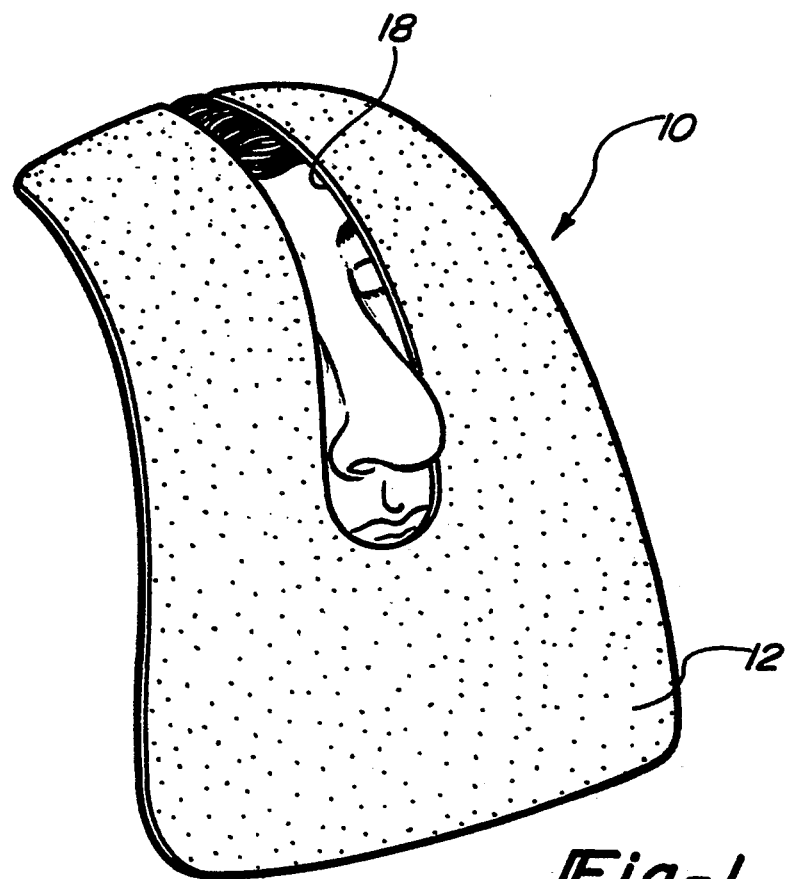
FIG. 1 is a perspective view of a drape sheet in accordance with the present invention illustrating a use of the drape sheet on the face of a patient.

Referring to FIG. 1, there is depicted therein a drapery shield in accordance with the present invention and generally denoted at 10. The shield 10 has an opening 18 formed therein which is to be placed about the area to be cauterized to provide exposure thereto.

Figure 2:
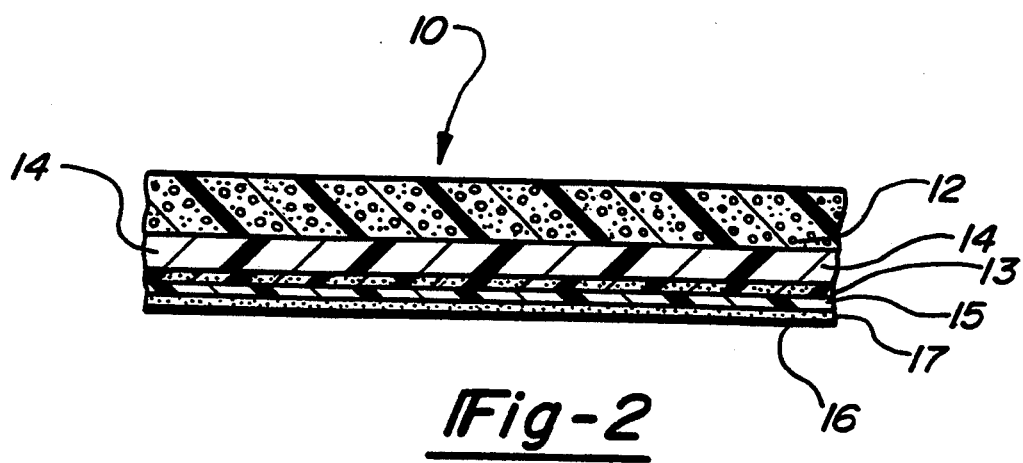
FIG. 2 is a cross-sectional view of the drape sheet illustrated in FIG. 1.

As depicted in FIG. 2, drapery shield 10 generally comprises a first or upper layer 12 made from a fire-retardant material; a second layer or underdrape 14, a paper backing 13, and an adhesive generally denoted at 16, for removably adhering the shield 10 about that area of a patient that is to be cauterized.

More particularly, the upper or first layer 12 is outwardly facing; i.e. exposed to the environment and is, preferably, as noted, formed from a fire-retardant foam. The fire-retardant foam prevents the cautery burning the face or other body part of the patient.

In accordance herewith, the fire-retardant foam may be formed from any suitable material, such as a polyurethane foam or the like. Fire-retardant polyurethane foams are well known and commercially available. Polyurethane foams have been described in the prior art, such as is found in U.S. Pat. Nos. 4,908,161, etc. It is to be understood that the present invention is not limited to any specific type of foam, other than the fact that it must be fire-retardant and must withstand the temperatures generated by a cautery. Likewise, the foam must be capable of being bonded or otherwise secured to the underdrape 14. Thus, any type of foam meeting these criteria may be used herein, e.g. isocyanurate foam, urea modified urethane foams, and the like.

Generally, the upper layer is a thin layered foam and is flexible to enable the shield to be easily folded and emplaced. Generally, a thickness of about 0.04 inches (1.00 mm).

The underdrape or second layer 14 is, preferably, a fluid impervious material, such as a polyethylene, polypropylene, nylon film, or the like. The second layer is non-porous and functions as an underdrape and covers the area around the opening to which the cautery will be applied. By being non-porous the flow of blood or other body fluids therepast is precluded.

The upper and lower layers are bonded to each other by any suitable mode, such as by heat bonding, sonic welding, gluing, or the like.

The shield 10 is held in place about the area to be cauterized by the adhesive 16. The adhesive 16 generally comprises an adhesive tape 15 or similar type of surgical tape which is well known in the art. Typically, a removable covering 17, covers the adhesive layer until it is ready for use.

Figure 3:
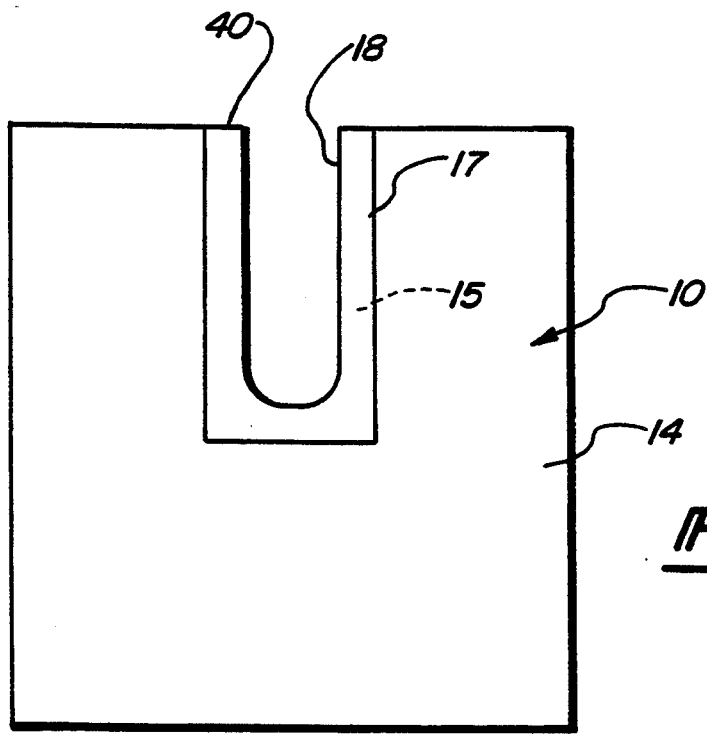
FIG. 3 is a rear plan view of the sheet shown in FIG. 2.
Figure 4:
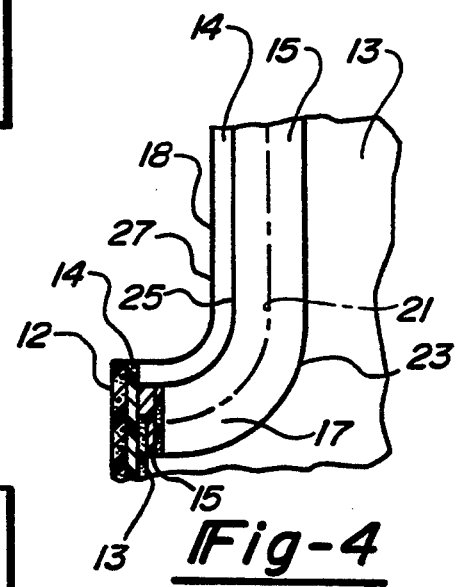
FIG. 4 is an enlarged fragmentary and partially segmented view illustrating the tape about the opening.

As shown in FIG. 3, the tape 15 and cover 17 are positioned on layer 14 only about the periphery of opening 18. The side of the tape 15 may be about 1"-2" (2.54-5.08 cm.) wide.

In use, the opening 18 is placed about the area to be cauterized, the covering 17 for the means 16 is removed and the shield is removably adhered via tape 15 about the area to be cauterized. The tape is loosely adhered to the patient's skin. The cautery may then be used substantially with inpugnity since the fire-retardant foam layer 12 will prevent burns to the face of the patient.

The optional paper backing 13 may be adhered to the rear surface of layer 14. The inner edge 21 of layer 13 may be positioned under the tape such that the one edge 23 of tape 15 is in contact with layer 13 and the second edge 25 is in adhesive contact directly with layer 14. The edge 25 may also be spaced lightly from the edge 27 of opening 18. After the cautery has been used, the shield is easily removed from the patient by merely stripping away the tape 15.

It is to be noted herein that the underdrape or second layer 14 is, also, a flexible thin layer having a thickness of about 0.02 inches (0.5 mm), thereby, rendering the entire drape foldable, pliable and easily usable.

Because of the nature of the materials employed in the manufacture of the shield, it is easily disposable.

Figure 5:
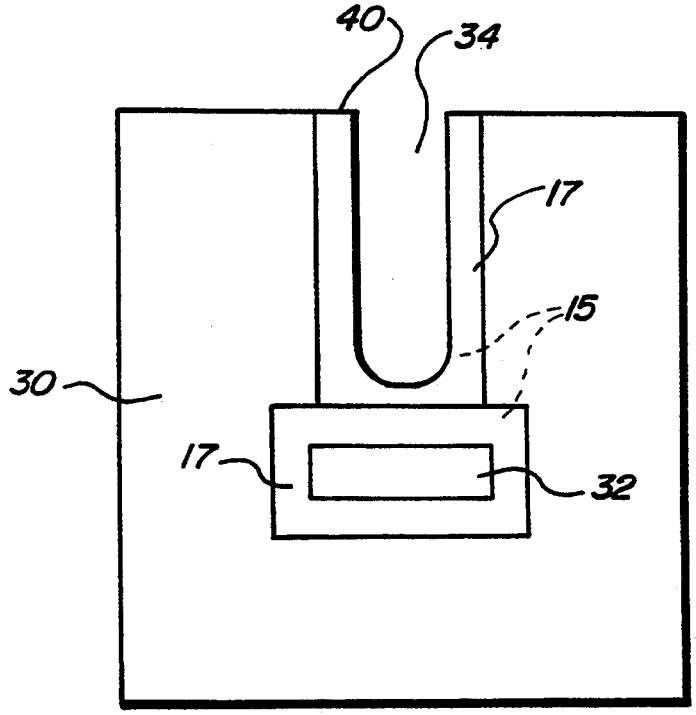
FIG. 5 is a front plan view illustrating an alternate embodiment.

FIG. 5 shown an alternate embodiment 30 with an opening 32 used for access to a patient's mouth. The opening 34 is provided for the patients nose to enable the patient to easily breath. Opening 34 is a slot extending from periphery 40 of the shield 30. Opening 32 is axially aligned with the slot. The tape 15 and cover 17 are positioned about both openings 32 and 34. The use of shield 30 is similar to shield 10.

It is to be appreciated from the preceding, that there has been described herein a drapery shield which effectively precludes cautery burns and the like.

Variations and modifications are possible without departing from the scope and spirit of the present invention as defined by the appended claims.

I claim:

1. A drapery shield for preventing cautery burns to that area of a patient, said shield comprising:
    a first layer of a fire-retardant material;
    an underdrape comprising a non-porous material;
    a first opening is provided in the shield to enable a patient to breath therethrough when placed on the face of a user;
    said first opening being in the form of a slot extending from a periphery of said shield sized to receive a nose of a patient;
    a second opening spaced axially aligned with and laterally spaced below said first opening opposite the periphery and positioned to provide access through a mouth of said patient;
    an adhesive positioned about said first and second openings for removably adhering the shield to said patient about his nose and mouth.

2. A shield as defined in claim 1 wherein the adhesive for removably adhering comprises an adhesive tape.

3. A shield as defined in claim 1 wherein said adhesive tape is positioned about said opening.

4. A shield as defined in claim 1 wherein the fire-retardant material is a fire-retardant polyurethane foam.

5. A shield as defined in claim 4 wherein the second layer is selected from the group consisting of non-porous polyethylene and non-porous polypropylene.

6. A shield as defined in claim 5 wherein the adhesive for removably adhering is n adhesive tape.

7. A shield as defined in claim 1 wherein the second layer of non-porous material is selected from the group consisting of polyethylene and polypropylene.

* * * * *